US00PP07916P

United States Patent [19]

Delbard

[11] Patent Number: Plant 7,916

[45] Date of Patent: Jul. 21, 1992

[54] ROSE PLANT—DELTESSE VARIETY

[75] Inventor: Georges Delbard, Malicorne, France

[73] Assignee: Georges Delbard Société Civile Agricole, Malicorne, France

[21] Appl. No.: 578,781

[22] Filed: Sep. 7, 1990

[51] Int. Cl.[5] ..... A01H 5/00

[52] U.S. Cl. ..... Plt./18

[58] Field of Search ..... Plt./11, 18

*Primary Examiner*—Howard J. Locker

*Attorney, Agent, or Firm*—Burns, Doane, Swecker & Mathis

[57] ABSTRACT

A new and distinct variety of hybrid tea rose plant is provided which abundantly forms attractive double white flowers which exhibit a hint of pink towards the center. Such flowers are long lasting and comprise petals which detach cleanly. The plant exhibits an upright to bushy growth habit, forms vigorous vegetation, and is well suited for greenhouse forcing for cut flower production. Additionally, the plant is not particularly susceptible to diseases.

1 Drawing Sheet

SUMMARY OF THE INVENTION

The new variety of hybrid tea rose plant was discovered while growing in a greenhouse among plants of the Delic variety (U.S. Plant Pat. No. 4,440). The Delic variety is marketed in Europe under the Eterna trademark. Such plants were being grown by Georges Delbard Société Civile for cut flower production at Hyéres, France. The new variety is believed to have been the result of a spontaneous mutation of unknown causation. I was primarily attracted to the new variety because of its distinctive flower coloration. More specifically, the flowers of the parent Delic variety possessed the usual clear and uniform pink coloration and the flowers of the new variety consistently possessed an attractive white coloration with only a hint of pink toward the center. Had the new variety not been discovered and preserved by me, it would have been lost to mankind.

The parentage of the parent Delic variety can be summarized as follows:

[(Michéle Meilland × Carla) × (Dr. Schweitzer × Tropicana] × (Queen Elizabeth × Provence).

Carla is the subject of U.S. Plant Pat. No. 2,401, Tropicana is the subject of U.S. Plant Pat. No. 1,969, and Queen Elizabeth is the subject of U.S. Plant Pat. No. 1,259.

It was found through careful study that the new variety of the present invention can be characterized by the following combination of characteristics:

(a) from a physical point of view it forms bronze green mature wood, assumes an upright to bushy growth habit, and forms attractive double white flowers with consistent petals having a hint of pink towards the center, and (b) from the biological point of view it forms vigorous vegetation, produces flowers in abundance, exhibits the ability readily to be forced, is not particularly susceptible to diseases, and forms long lasting flowers comprising petals which detach cleanly.

The new variety well meets the needs of the horticultural industry and is particularly well suited for cut flower production.

The new variety has been found to undergo asexual propagation and can be readily reproduced by conventional routes such as budding (i.e., eye grafting), the use of cuttings, and micropropagation in artificial media. Asexual propagation by the above-mentioned methods as performed in France has demonstrated that the characteristics of the new variety are strictly transmissible from one generation to another and appear to be firmly fixed.

The new variety has been named the Deltesse variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass at Hyéres, France.

DETAILED DESCRIPTION

Figures 1, 2, 3, 4, 5, 6, 7, 8, 9, 10, 11, 12, 13, 14, 15, 16:
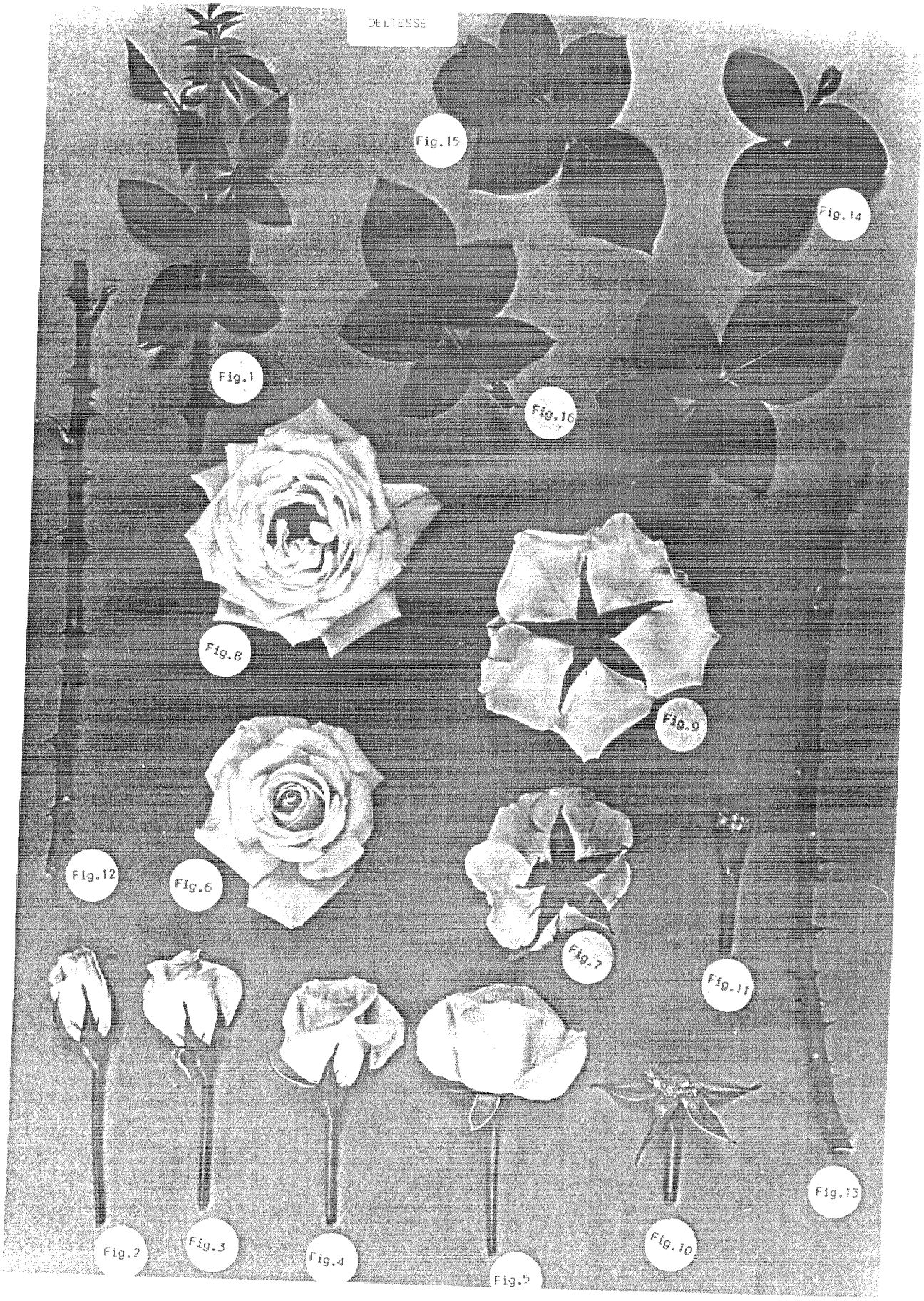
FIG. 1 illustrates a specimen of a young shoot.
FIG. 2 illustrates a specimen of a floral bud at the opening of the sepals.
FIG. 3 illustrates a specimen of a floral bud at the opening of the petals.
FIG. 4 illustrates a specimen of a flower in the course of opening.
FIG. 5 illustrates a specimen of a flower in a more advanced stage of opening.
FIG. 6 illustrates a specimen of an open flower — plan view — obverse.
FIG. 7 illustrate a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (sepals and stamens removed)
FIG. 12 illustrates a specimen of a flowering stem.
FIG. 13 illustrates a specimen of a main branch.
FIG. 14 illustrates a specimen of a leaf with three leaflets — plan view — upper surface.
FIG. 15 illustrates a specimen of a leaf with five leaflets — plan view — upper surface.
FIG. 16 illustrates specimens of two leaves with five leaflets — plan view — under surface.

The chart used in the identification of the colors is that of The Royal Horticultural Society (R.H.S. Colour Chart).

The description is based on the observation of plants grown under glass at Hyéres, France. The coloration in common terms sometimes also is provided.

Class: Hybrid tea.

Plant:

*Height.*—Plants which were pruned to a height of 85 cm. produce floral stems having a length of approximately 40 to 50 cm.

*Habit.*—Upright to bushy.

Branches:

*Color.*—Young shoots: when approximately 20 cm. long, sometimes exhibit a weak anthocyanin coloration. Such coloration commonly approximates that of the Yellow-Green Group 146B and is shaded with bronzy coloration. Floral stems: Yellow-Green Group 146B. Mature wood: bronze green. Yellow-Green Group 146A.

*Thorns.*—Configuration: concave upper and lower surfaces. Quality: few which are 5 mm. or less in length, and an average number which are greater than 5 mm. in length. Color: when present on young shoots having a length of approximately 20 cm., Yellow-Green Group 148A; when present on floral stems, Greyed-Orange Group 175B and 175C; and when present on mature wood, Greyed-Orange Group 166C and 166D.

*Petiole.*—Color on young shoots: Yellow-Green Group 146B on upper surface, and Yellow-Green Group 146B and 146C on under surface.

*Leaflets.*—Number: commonly 3 and 5. Size: medium. Shape: oval as illustrated, and convex with a weak margin undulation. Serration: single and regular. Texture: consistent. Color on young shoots: Yellow-Green Group 146A on upper surface, and Yellow-Green Group 146B shaded with brown and purple on under surface. Color on floral stems: Yellow-Green Group 147A on upper surface, and Yellow-Green Group 147A on under surface. Color on mature wood: Yellow-Green Group 147A on upper surface and Yellow-Green Group 147B on under surface. General appearance: a weak glossiness commonly is present on the upper surface of the leaflets. Terminal leaflets: medium in length and width, have a rounded base, and are borne on petioles of medium length.

Inflorescence:

*Number of flowers.*—Generally one per stem when grown under greenhouse conditions.

*Peduncle.*—Few or no hairs or prickles are present, and the coloration is Yellow-Green Group 146B and 146C.

Sepals.—Configuration: relatively long in length, with weak extensions. Color: Yellow-Green Group 146D on the upper surface, and Yellow-Green Group 146C on the under surface.

*Buds.*—Shape: ovate in longitudinal section just before the opening of the sepals.

*Flowers.*—Time: flowering begins early. Shape: double, generally round when viewed from above, a generally flat upper surface when viewed from the side, and a generally convex under surface when viewed from the side. Diameter: approximately 92–100 mm. when fully open. Petal size: at second row from outside approximately 50 to 60 mm. in length, and approximately 48 to 53 mm. in width. Petal shape: the first 2 to 3 well-developed outermost petals tend to be of a broad obovate configuration and may be removed and discarded, the margins possess very weak reflexing, and the margin undulation is weak. Petal color: the middle and marginal zones of the inner and outer sides are White Group 155D with a hint of Red Group 36D, and a spot tends to be absent from the inner and outer sides. Fragrance: slight. Lasting quality: long. Petal number: approximately 27 to 32 on average. Petal drop: good. Stamens: commonly number approximately 210, and are irregularly arranged around pistils. Filaments: length is short to medium, many lack anthers, and the predominant coloration is Yellow Group 2C. Anthers: medium in size, tend to open at substantially the same time, and the immature coloration approximates Yellow-Orange Group 19A. Pollen: is yellow in coloration and is provided in normal quantity. Pistils: commonly number approximately 67. Stigmas: generally of a lesser height than the anthers, the base is red in coloration, and the upper part approximates Yellow-Orange Group 14C in coloration. Styles: short to medium in length, the coloration is yellow, and commonly an average quantity of hairiness is present on the upper one-half. Receptacle: medium in size, approximately 32 mm. in diameter, and in longitudinal section it is in the shape of a pitcher.

Development:

*Vegetation.*—Vigorous.

*Blooming.*—Very abundant and almost continuous.

*Resistance to diseases.*—Good.

*Aptitude to forcing.*—Excellent.

*Seeds.*—Large in size and commonly number approximately 5 to 12.

Generally, one flower per stem is formed when the new variety is grown under greenhouse conditions. However, in some instances multiple buds per stem are observed.

Each of the parent varieties for the Deltesse variety forms flowers which possess a coloration other than white. For instance, the Michele Meilland variety forms light pink blossoms having a salmon center which are shaded with lilac, and Carla variety forms soft salmon pink blossoms, the Dr. Schweitzer variety forms opal-pink blossoms which are red on the underside, the Tropicana variety forms coral-orange blossoms, the Queen Elizabeth variety forms medium pink blossoms, and the Provence variety forms orange blossoms which are tinted with copper and pink.

I claim:

1. A new and distinct variety of hybrid tea rose plant characterized by the following combination of characteristics:

(a) from a physical point of view forms bronze green mature wood, assumes an upright to bushy growth habit, and forms attractive double white flowers with consistent petals having a hint of pink towards the center, and (b) from the biological point of view forms vigorous vegetation, produces flowers in abundance, exhibits the ability readily to be forced, is not particularly susceptible to diseases, and forms long lasting flowers comprising petals which detach cleanly;

substantially as herein shown and described.

* * * * *

DELTESSE